(12) United States Patent
Zhou et al.

(10) Patent No.: US 12,102,328 B2
(45) Date of Patent: Oct. 1, 2024

(54) LEFT ATRIAL APPENDAGE OCCLUDER AND LEFT ATRIAL APPENDAGE OCCLUSION SYSTEM

(71) Applicant: SHANGHAI MICROPORT CARDIOADVENT CO., LTD., Shanghai (CN)

(72) Inventors: Yi Zhou, Shanghai (CN); Haiyong Huang, Shanghai (CN); Shaoyang Liu, Shanghai (CN); Yao Yao, Shanghai (CN); Junfei Li, Shanghai (CN)

(73) Assignee: SHANGHAI MICROPORT CARDIOADVENT CO., LTD., Shanghai (CN)

( * ) Notice: Subject to any disclaimer, the term of this patent is extended or adjusted under 35 U.S.C. 154(b) by 350 days.

(21) Appl. No.: 17/277,527

(22) PCT Filed: Sep. 11, 2019

(86) PCT No.: PCT/CN2019/105322
§ 371 (c)(1),
(2) Date: Mar. 18, 2021

(87) PCT Pub. No.: WO2020/063348
PCT Pub. Date: Apr. 2, 2020

(65) Prior Publication Data
US 2022/0031333 A1 Feb. 3, 2022

(30) Foreign Application Priority Data
Sep. 29, 2018 (CN) .......................... 201811150646.2

(51) Int. Cl.
*A61B 17/12* (2006.01)

(52) U.S. Cl.
CPC .. *A61B 17/12122* (2013.01); *A61B 17/12172* (2013.01); *A61B 2017/1205* (2013.01)

(58) Field of Classification Search
CPC ........ A61B 17/12122; A61B 17/12172; A61B 2017/1205; A61B 17/0057; A61B 2017/00243
See application file for complete search history.

(56) References Cited

U.S. PATENT DOCUMENTS

| | | | |
|---|---|---|---|
| 2014/0135817 A1 | 5/2014 | Tischler et al. | |
| 2014/0364941 A1* | 12/2014 | Edmiston | A61B 17/12177 623/2.11 |
| 2016/0066922 A1* | 3/2016 | Bridgeman | A61B 17/0057 606/200 |

FOREIGN PATENT DOCUMENTS

| CN | 103845096 A | 6/2014 |
|---|---|---|
| CN | 104352261 A | 2/2015 |

(Continued)

*Primary Examiner* — Todd J Scherbel
(74) *Attorney, Agent, or Firm* — MUNCY, GEISSLER, OLDS & LOWE, P.C.

(57) ABSTRACT

A left atrial appendage (LAA) occluder and an LAA occlusion system are disclosed. The LAA occluder enables an increased surgical success rate by allowing repeated good positioning, retrieval and release of the occluder and avoiding the problem of entanglement of the occluding stent during surgery. The LAA occluder includes an occluding stent, a proximal securing member a distal securing member. The occluding stent includes an occlusion structure and a traction structure. The delivery device includes a hollow push tube and a control shaft. The distal securing member can be driven by the control shaft to move toward the proximal securing member until a first distal end of the occlusion structure is in a collapsed configuration, where the distal securing member is blocked from further movement, avoiding the problem of entanglement arising from inward rolling of the occluding stent in the vent of human error.

18 Claims, 7 Drawing Sheets

(56) References Cited

FOREIGN PATENT DOCUMENTS

| | | | |
|---|---|---|---|
| CN | 105596052 | A | 5/2016 |
| CN | 105662647 | A | 6/2016 |
| CN | 104168843 | A | 11/2016 |
| CN | 205729416 | U | 11/2016 |
| CN | 107126241 | A | 9/2017 |
| CN | 108236479 | A | 7/2018 |
| CN | 108420469 | A | 8/2018 |
| JP | 2005515830 | A | 6/2005 |
| JP | 2011161233 | A | 8/2011 |
| JP | 2014534872 | A | 12/2014 |
| WO | WO2008150346 | A1 | 12/2008 |
| WO | WO-2013/067188 | A1 | 5/2013 |
| WO | WO2015070733 | A1 | 5/2015 |
| WO | WO2015135369 | A1 | 9/2015 |
| WO | WO2017214577 | A1 | 12/2017 |

\* cited by examiner

LEFT ATRIAL APPENDAGE OCCLUDER AND LEFT ATRIAL APPENDAGE OCCLUSION SYSTEM

TECHNICAL FIELD

The present invention relates to the field of implantable medical devices and, in particular, to a left atrial appendage (LAA) occluder and an LAA occlusion system including the LAA occluder.

BACKGROUND

Atrial fibrillation (AF) is the most common perpetual arrhythmia seen in clinical practice and is associated with a risk of causing ischemic stroke. Therefore, the prevention of atrial fibrillation is of great significance. Recent studies have shown that LAA occlusion is an effective countermeasure to the risk of AF-caused ischemic stroke.

Existing LAA occluders can be generally categorized into one-piece and two-piece ones. Watchman occluders are typical one-piece LAA occluders, which feature a cage-like shape and an integral skeleton. Such occluders are easy to fabricate and can be implanted so as to be entirely anchored in the LAA. Representative examples of two-piece LAA occluders include LAmbre occluders. Such occluders are characterized in consisting of a locator and an occluding disc connected to the locator. In use, the locator is anchored in the LAA and functions like a rivet. LAA occlusion is primarily accomplished by the occluding disc secured at the LAA orifice, although the locator also makes a certain contribution to the occlusion.

However, occluders of both types do not allow passage of a guide wire therethrough, leading to the following two common disadvantages: 1) implantation of the occluder must follow withdrawal of the guide wire from a sheath and rely on position by the sheath, which brings great challenges to the design of the sheath, limits its other capabilities, raises its cost and tends to cause straightening and hence an unfavorable orientation of the sheath due to the passage of a stent therethrough or release of the stent; and 2) once decoupled and released, retrieval of the occluder is difficult and has to rely on the use of a snare, which is, however, associated with a very low success rate.

There, there is still a need in the art for an occluder allowing easy passage, position and orientation, as well as easy retrieval after it is deployed.

SUMMARY OF THE INVENTION

It is an objective of the present invention to disclose a left atrial appendage (LAA) occluder and an LAA occlusion system including the LAA occluder, which allows re-positioning, release and orientation of the LAA occluder and an increased surgical success rate.

It is another objective of the present invention to disclose an LAA occluder and an LAA occlusion system including the LAA occluder, which allows easy retrieval of the LAA occluder without using a snare after it is released, and hence increased utilization efficiency thereof.

The above objectives are attained by an LAA occluder according to the present invention, which includes an occluding stent, a proximal securing member and a distal securing member. The occluding stent includes an occlusion structure and a traction structure. The occlusion structure has a first proximal end and a first distal end opposing the first proximal end. The proximal securing member is disposed at the first proximal end and configured to form a closed configuration at the first proximal end, and the first distal end is configured in an open configuration. The traction structure is connected to the occlusion structure and is at least partially overlapped with the occlusion structure along an axial direction, the traction structure comprising a plurality of traction elements each having a first end connected to the distal securing member and a second end connected to the occlusion structure, wherein movement of the distal securing member toward the proximal securing member is able to cause the occluding stent to transition from an expanded configuration to a collapsed configuration. The collapsed configuration includes, but is not limited to, mutual approaching of portions at the first distal end, abutting of them against one another, crossing of them over one another and partial or entire inward rolling of them.

Preferably, the occlusion structure may be divided by the traction structure into a first portion and a second portion joined to the first portion along the axial direction, wherein the first portion provides the first proximal end, and the second portion provides the first distal end.

Preferably, a length of the second portion may be equal to 3% to 30% of an outer diameter or total length of the occlusion structure.

Preferably, the length of the second portion may be equal to 5% to 25% of the outer diameter or total length of the occlusion structure.

Preferably, the length of the second portion may be equal to 8% to 22% of the outer diameter or total length of the occlusion structure.

Preferably, the length of the second portion may be equal to 10% to 20% of the outer diameter or total length of the occlusion structure.

Preferably, the length of the second portion may be equal to 10%, 11%, 12%, 13%, 14%, 15%, 16%, 17%, 18%, 19% or 20% of the outer diameter or total length of the occlusion structure.

Preferably, the length of the second portion may correspond to 0.1 to 1.0 segment.

Preferably, the length of the second portion may correspond to 0.2 to 0.9 segment.

Preferably, the length of the second portion may correspond to 0.3 to 0.8 segment.

Preferably, the length of the second portion may correspond to 0.3, 0.4, 0.5, 0.6, 0.7 or 0.8 segment.

Preferably, the second portion may be one or a combination of a tapered structure, a straight structure and a flared structure.

Preferably, a distalmost end of the second portion may be a tapered structure.

Preferably, the LAA occluder may further include a hollow guide member coupled to the occlusion structure, wherein the hollow guide member is arranged coaxially with the proximal securing member so as to allow passage of the distal securing member and at least part of the traction structure therethrough.

Preferably, the hollow guide member may have a second proximal end and a second distal end opposing the second proximal end, wherein the second proximal end is coupled to the first proximal end of the occlusion structure, and wherein the distal securing member and the at least part of the traction structure are able to be inserted into the hollow guide member from the second distal end, the second distal end having a flared opening.

Preferably, the hollow guide member may have an inner diameter smaller than the length of the second portion.

Preferably, the traction structure may be completely overlapped with the occlusion structure along the axial direction.

Preferably, the occlusion structure may further include a plurality of projections at the first distal end, the plurality of projections abutting against one another, to limit the movement of the distal securing member toward the proximal securing member under traction of the traction structure.

Preferably, a connection point of the traction structure to the occlusion structure may be aligned with the distal securing member along the axial direction.

Preferably, the occlusion structure may include a plurality of mesh cells, the plurality of mesh cells each having a plurality of corner nodes, and wherein a number of the traction elements is smaller than or equal to that of the plurality of corner nodes on a same circumference of the occlusion structure.

Preferably, the number of the traction elements may be at least three.

Preferably, the LAA occluder may further include an occluding membrane, which covers at least part of an internal or external surface of the occluding stent.

Preferably, the occlusion structure and/or the traction structure may be provided thereon with an anchor for securing the left atrial appendage occluder to an inner wall of a left atrial appendage.

Preferably, the occlusion structure may be molded integrally with, or separately from, the traction structure, wherein the distal securing member is arranged coaxially with the proximal securing member.

The above objectives are also attained by an LAA occlusion system including the LAA occluder as defined in any of the above paragraphs and a delivery device. The delivery device includes a hollow push tube and a control shaft. The hollow push tube is detachably coupled to the proximal securing member in order to allow delivery and release of the LAA occluder, and the control shaft is inserted through the hollow push tube and the proximal securing member and is detachably coupled to the distal securing member in order to allow retrieval and release of the LAA occluder.

Preferably, the hollow push tube may have a third distal end configured for connection with the proximal securing member by threading, latching or snapping, and the control shaft may have a fourth distal end configured for connection with the distal securing member by threading, latching or snapping.

In the above-described LAA occluder and LAA occlusion system including the LAA occluder, each of the occlusion and traction structures of the occluding stent is coupled to a respective one of the securing members (wherein the distal securing member coupled to the traction structure is moveable relative to the proximal securing member coupled to the occlusion structure). In this way, the axial length of the occluding stent can be shortened, resulting in a reduced length of the delivery device, lowered cost, reduced surgical difficulty and a shorter surgical time. Moreover, according to the present invention, in addition to a reduction in the axial length of the occluding stent, the movement of the distal securing member toward the proximal securing member can also result in a reduced outer diameter of the occluding stent, which can facilitate retrieval of at least part of the occluding stent into the delivery sheath during release and subsequent re-positioning and re-release thereof. Additionally, this can keep the anchors on the occluding stent away from the inner wall of the LAA under the action of the distal securing member, avoiding bringing damage to the tissue or muscle during repeated re-positioning and retrieval and assuring safety and reliability of the retrieval operation. Notably, according to the present invention, when the end portions of the occlusion structure at the first distal end are gathered to abut against, or even cross over, one another as a result of the movement of the distal securing member toward the proximal securing member, further movement of the distal securing member (i.e., further retraction of the control shaft) will be blocked. This can avoid the problem of entanglement resulting from inward rolling of the occluding stent in the event of human error, resulting in an additional increase in surgical success rate.

Furthermore, according to the present invention, controlling the deformation of the LAA occluder by means of the control shaft that is independent of the hollow push tube can simplify and facilitate the retrieval operation. Additionally, according to the present invention, the retrieval operation is made even easier and more convenient by limiting the direction of movement of the distal securing member with the hollow guide member coupled to the occlusion structure. This also facilitates the inward rolling of the second portion of the occlusion structure under the traction of the traction structure and consequent direct abutting against the distal end of the hollow guide member, which prevents further entry of the second portion into the hollow guide member, thus allowing more effective blocking of further retraction of the control shaft.

BRIEF DESCRIPTION OF THE DRAWINGS

It will be appreciated by those of ordinary skill in the art that the accompanying drawings are provided for a better understanding of the present invention and do not limit it in any way. In these figures.

In these figures,

100-LAA occluder; 110, 10-occluding stent; 111-occlusion structure; 111a-first proximal end; 111b-first distal end; 111c-first portion; 111d-second portion; 112-traction structure; 1121-traction element; 113, 11-anchor; 120-proximal securing member; 130-distal securing member; 140-occluding membrane; 150-hollow guide member;
200-delivery device;
210-hollow push tube; 211-third distal end;
220-control shaft; 221-fourth distal end.

In these figures, like components are indicated by like reference numerals.

DETAILED DESCRIPTION

Objectives, advantages and features of the present invention will be more apparent from the following more detailed description thereof, which is to be read in conjunction with the accompanying drawings. It is noted that the figures are provided in a very simplified form not necessarily presented to scale, with their only intention to facilitate convenience and clarity in explaining the disclosed embodiments.

As used herein and in the appended claims, the singular forms "a", "an", and "the" include plural references unless the context clearly dictates otherwise. As used herein and in the appended claims, the term "or" is generally employed in its sense including "and/or" unless the content clearly dictates otherwise.

In the following description, the terms "distal", "proximal", "axial" and "circumferential" are used for the sake of ease of description. A "distal" end of a delivery device is meant to refer to its end located farther away from a left atrial appendage (LAA) occluder, and a "proximal" end of the delivery device is meant to refer to its end located closer to the LAA occluder. The term "axial" is used to describe the direction along an axis of an occluding stent in the LAA occluder, and the term "circumferential" is used to describe the direction about the axis of the occluding stent in the LAA occluder. The term "inward" is intended to mean a direction pointing toward the axis of the occluding stent, while the term "outward" is meant to mean a direction opposite to the direction that the term "inward" is intended to mean. In addition, the terms "first", "second" and "third" are used only for the purpose of illustration and are not to be construed as indicating or implying relative importance or implicitly indicating the number of the stated features. Therefore, a feature described with the term "first", "second" or "third" can explicitly or implicitly indicate the presence of one or more such features. As used herein, the term "plurality" has the meaning of "two or more", unless the context clearly indicates otherwise.

Further, the following description sets forth numerous specific details in order to provide a more thorough understanding of the present invention. However, it will be apparent to those skilled in the art that the present invention can be practiced without one or more of these specific details. In other instances, well-known technical features have not been described in order to avoid unnecessary obscuring of the present invention.

Figure 1:
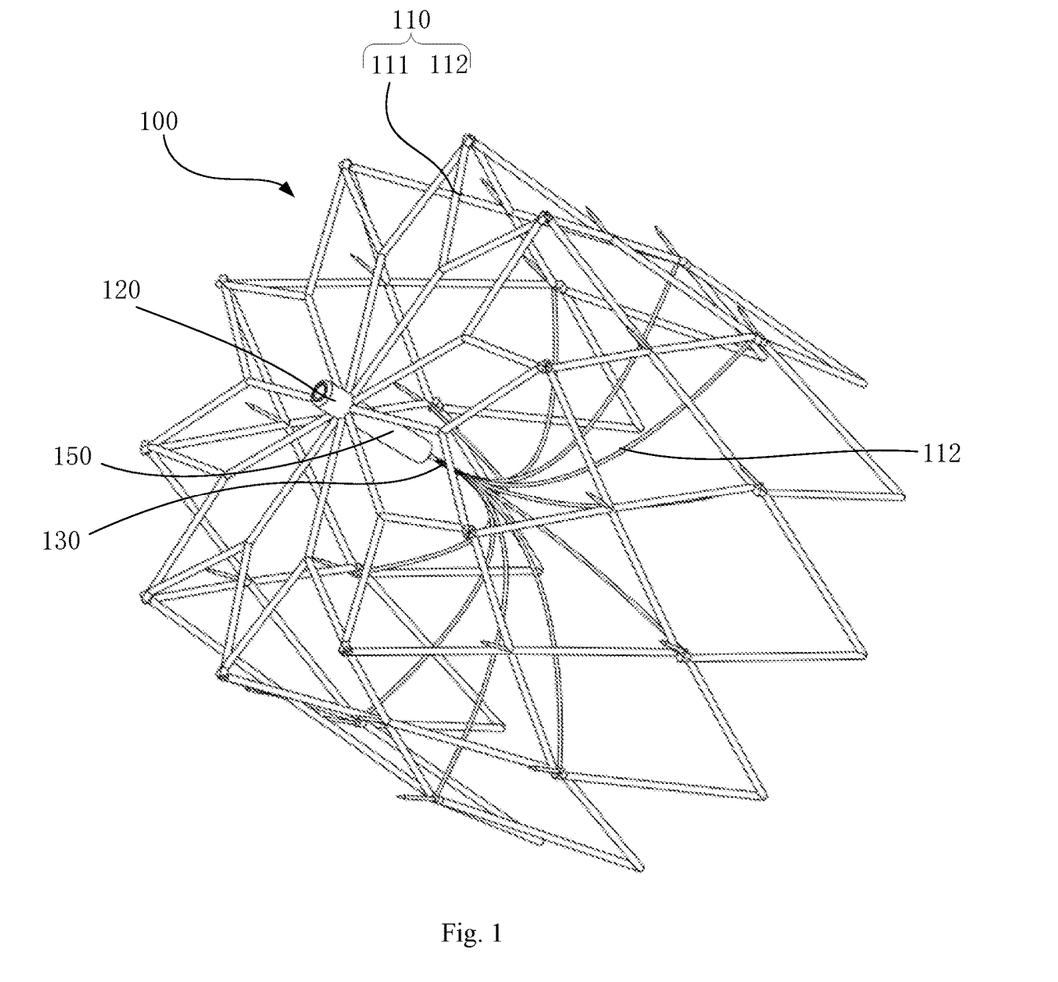
FIG. 1 is a schematic perspective view of a left atrial appendage (LAA) occluder according to an embodiment of the present invention.
Figure 2:
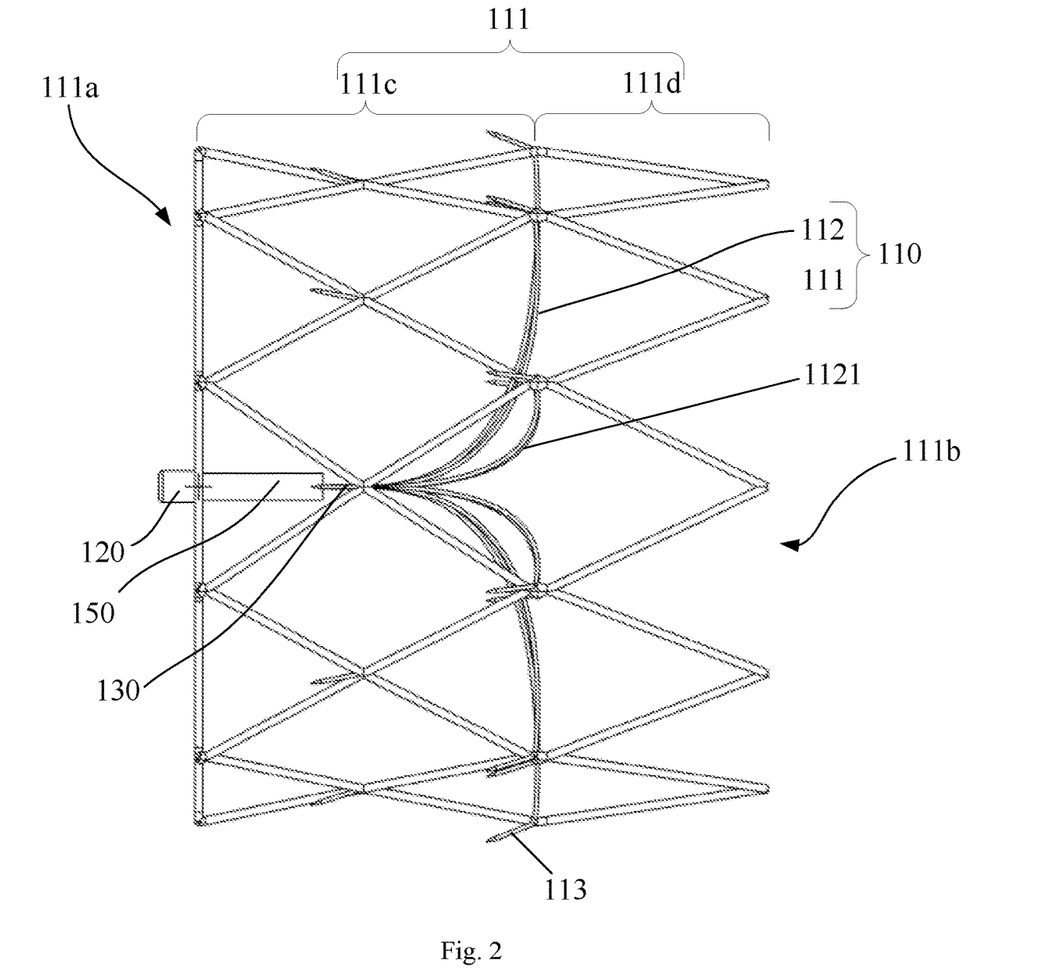
FIG. 2 is a side view of the LAA occluder of FIG. 1.

A detailed description is given below with reference to the accompanying drawings. FIG. 1 is a schematic perspective view of a left atrial appendage (LAA) occluder according to an embodiment of the present invention, and FIG. 2 is a side view of the LAA occluder of FIG. 1. As shown in FIGS. 1 and 2, the LAA occluder 100 includes an occluding stent 110, a proximal securing member 120 and a distal securing member 130.

The occluding stent 110 includes an occlusion structure 111 and a traction structure 112. The occlusion structure 111 is in the form of a tubular mesh and has a first proximal end 111a and a first distal end 111b opposing the first proximal end 111a. The proximal securing member 120 is arranged at the first proximal end 111a and is configured to form a closed configuration at the first proximal end 111a. Specifically, this can be accomplished by gathering end portions of the occlusion structure 111 at the first proximal end 111a to the proximal securing member 120. The first distal end 111b is configured in an open configuration. Specifically, a portion of the occlusion structure 111 around the first distal end 111b is configured to form an opening. The traction structure 112 is attached to the occlusion structure 111. Preferably, the connection point of the traction structure 112 to the occlusion structure 111 forms a boundary that axially divides the occlusion structure 111 into two parts. Here, the traction structure 112 may be attached to the occlusion structure 111 either fixedly, for example, by welding, integral molding, etc., or movably, for example, by disposing one end of the traction structure over the occlusion structure 111. Moreover, in some embodiments, the traction structure 112 may be completely overlapped with the occlusion structure 111 across its axial length. In other embodiments, the traction structure 112 may be partially overlapped with the occlusion structure 111 across its axial length. Here, the term "completely overlapped" means that the traction structure 112 is entirely disposed within the occlusion structure 111, while "partially overlapped" means that part of the traction structure 112 is disposed within the occlusion structure 111, while the remainder extends out of the occlusion structure 111 at the first distal end 111b thereof.

The traction structure 112 includes a plurality of traction elements 1121, each having a first end connected to the distal securing member 130, preferably by welding or crimping, and a second end connected to the occlusion structure 111. Preferably, the second ends of all the traction elements 1121 are distributed about an axis of the occlusion structure 111. For easier operation, the distal securing member 130 is preferably disposed coaxially with the proximal securing member 120.

Figure 3:
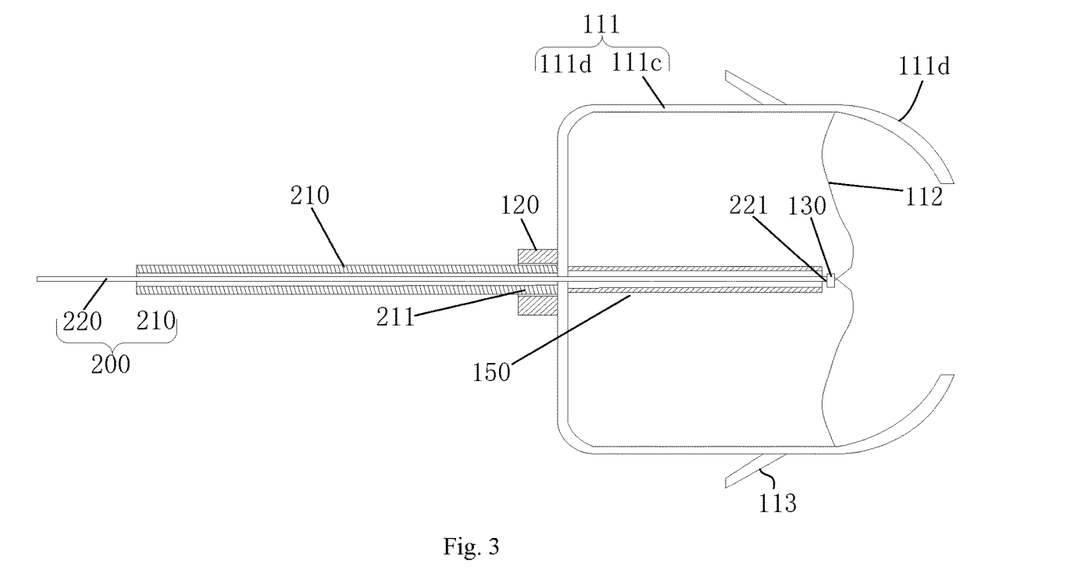
FIG. 3 is a schematic diagram of an LAA occluder and a delivery device coupled thereto according to an embodiment of the present invention, in which end portions of the LAA occluder at a first distal end thereof are not gathered yet.
Figure 4A:
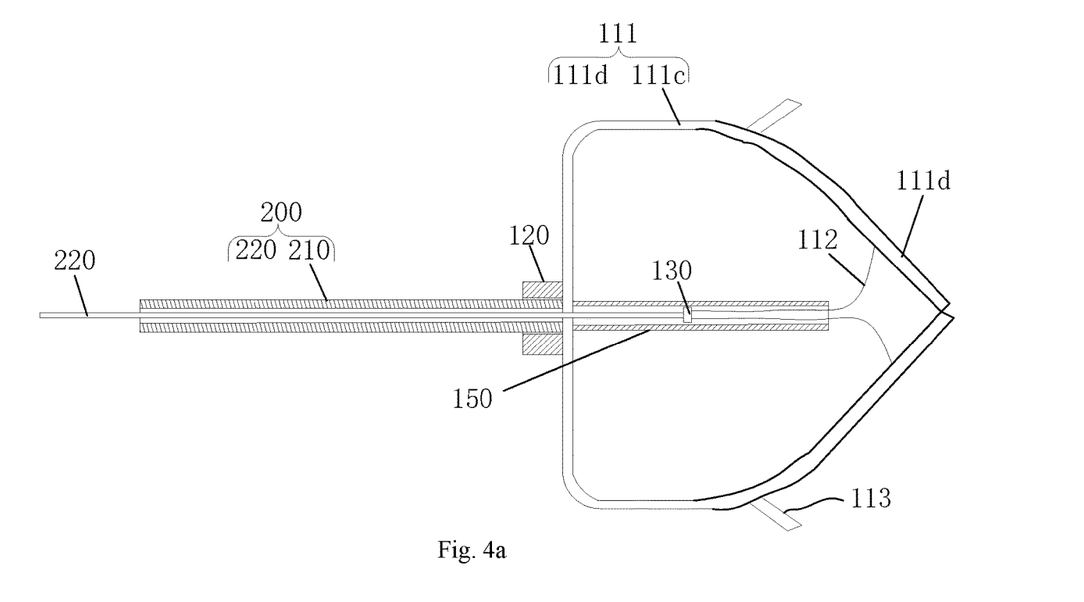
FIG. 4a is a schematic diagram of the LAA occluder of the FIG. 3, with its end portions at the first distal end being gathered to abut against one another as a result of a driving action of the delivery device.
Figure 4B:
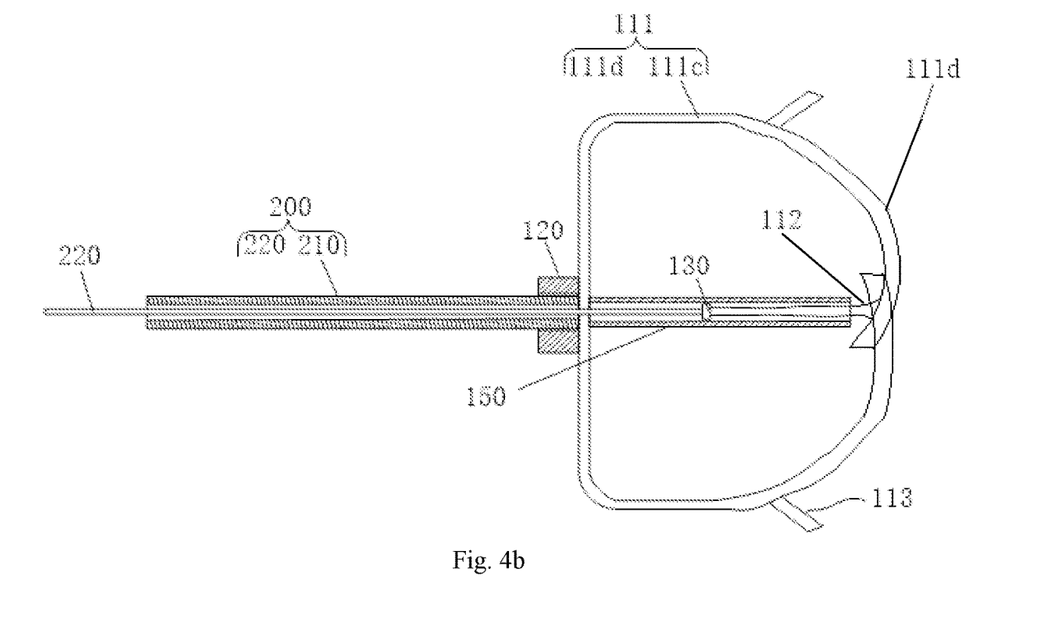
FIG. 4b is a schematic diagram of the LAA occluder of the FIG. 3, with its end portions at the first distal end being gathered to cross over one another as a result of a driving action of the delivery device.

Reference is now made to FIGS. 3, 4a and 4b. FIG. 3 schematically illustrates an LAA occluder according to an embodiment of the present invention and a delivery device coupled thereto. FIG. 4a schematically illustrates the LAA occluder of FIG. 3 with end portions thereof at the first distal end being gathered under action of the delivery device to abut against one another. FIG. 4b schematically illustrates the LAA occluder of FIG. 3 with the end portions thereof at the first distal end being gathered under action of the delivery device to cross over one another.

As shown in FIGS. 3, 4a and 4b, the delivery device 200 may include a hollow push tube 210 and a control shaft 220. The hollow push tube 210 may have a third distal end 211 complementary in form to the proximal securing member 120 so that the hollow push tube 210 can be detachably coupled to the occluding stent 110 to allow delivery and release of the LAA occluder. The proximal securing member 120 may define a hollow lumen so that the control shaft 220 can pass through both the hollow push tube 210 and the proximal securing member 120 and come into the detachable connection with the distal securing member 130 when protruding out of the proximal securing member 120. In this way, retrieval and release of the LAA occluder can be accomplished with the control shaft 220 (in this case, the hollow guide member 150 in the figure can be omitted, and the case with the hollow guide member 150 will be described in detail later).

In this design, the control shaft 220 can be manipulated to pull the distal securing member 130 to cause its movement relative to the proximal securing member 120. As a result, the occluding stent 110 will collapse or expand at the first distal end 111b, under the control of the control shaft 220. Preferably, movement of the distal securing member 130 toward the proximal securing member 120 can cause the end portions of the occluding stent 110 at the first distal end 111b to abut against one another, as shown in FIG. 4a or 4b.

With reference to FIGS. 3 and 4a, when the control shaft 220 is retracted toward the first proximal end 111a of the occlusion structure 111, the distal securing member 130 will be driven to move toward the proximal securing member 120, causing inward rolling of the end portions of the occluding stent 110 at the first distal end 111b. Moreover, when the control shaft 220 is retracted to an appropriate position, the end portions of the occlusion structure 111 at the first distal end 111b will abut against one another. In this configuration, the abutting of the end portions of the occluding stent 110 at the first distal end 111b against one another will stop further retraction of the control shaft 220 and hence further inward rolling of the occluding stent 110, thus avoiding entanglement between opposite sides of the concave-shaped occluding stent that may be caused by the further retraction.

More specifically, before the collapse, as shown in FIG. 2, the occlusion structure 111 may be divided by the traction structure 112 into a first portion 111c and a second portion 111d axially joined to the first portion 111c. That is, with the connection point of the traction structure 112 to the occlusion structure 111 being considered as a boundary, the first portion 111c is located on one side of the boundary, and the second portion 111d is located on the other side of the boundary. Moreover, the first portion 111c may provide the first proximal end 111a, and the second portion 111d may provide the first distal end 111b. The first and second portions 111c, 111d may be separately fabricated and then both connected to the traction structure 112. Alternatively, the first and second portions 111c, 111d may be connected together or integrally molded, followed by attachment of the traction structure 112 to them. Still alternatively, the first portion 111c, the second portion 111d and the traction structure 112 may be molded as a unitary structure. The present invention is not limited to any particular method for attaching the traction structure 112 to the occlusion structure 111. The traction structure 112 may be attached to the occlusion structure 111 by suturing, welding, bonding, snapping or the like.

In addition, the second portion 111d may be tapered, as shown in FIG. 3. Although not shown, it may also be straight or flared. Still alternatively, it may consist of a combination of any two or three of a tapered section, a straight section and a flared section. For example, the second portion 111d may consist of a flared section at its proximal end, a tapered section at its distal end, and a straight section between the two. The flared section may have a cross-sectional area increasing in the direction from the proximal to distal end of the second portion 111d. The straight section may have a cross-sectional area unchanged in the direction from the proximal to distal end of the second portion 111d. The tapered section may have a cross-sectional area decreasing in the direction from the proximal to distal end of the second portion 111d. Preferably, the second portion 111d is made up of a single tapered section, or has a tapered section at the distal end, in order to avoid piercing and tearing tissue. Further, an excessively small inward taper angle of the tapered section tends to cause damage to tissue and should be avoided. Of course, an excessively large inward taper angle of the tapered section should also be avoided, because it tends to cause entanglement of the end portions at the first distal end during their gathering.

Further, the second portion 111d may in particular have a plurality of projections at the first distal end 111b, which will abut against one another as a result of movement of the distal securing member 130 toward the proximal securing member 120 under the traction of the traction structure 112. The projections may be in the shape of triangles, but the present invention is not so limited, because the projections may also be in the shape of trapezoids, rectangles, waves or the like. In one embodiment, the projections are defined by a number of mesh cells of the second portion 111d. For example, as shown in FIG. 1, the projections may be provided by triangular portions of diamond-shaped mesh cells, which are distributed at the first distal end 111b on the circumference of a circle. Additionally, the second portion 111d is preferred to have a length that is equal to 3% to 30% of an outer diameter or total length of the occlusion structure 111, in order to ensure effective abutting at the first distal end 111b. In some embodiments, the length of the second portion 111d may be equal to 5% to 25% of the outer diameter or total length of the occlusion structure 111. In some embodiments, the length of the second portion 111d may be equal to 8% to 22% of the outer diameter or total length of the occlusion structure 111. In some embodiments, the length of the second portion 111d may be equal to 10% to 20% of the outer diameter or total length of the occlusion structure 111. In some embodiments, the length of the second portion 111d may be equal to 10%, 11%, 12%, 13%, 14%, 15%, 16%, 17%, 18%, 19% or 20% of the outer diameter or total length of the occlusion structure 111. The length of the second portion 111d may be equal to, for example, 0.1 to 1 segment width or in any range between those values. Here, the term "segment width" refers to an axial length of each mesh cell of the occlusion structure. In some embodiments, the length of the second portion 111d may be equal to, for example, 0.2 to 0.9 segment widths. In some embodiments, the length of the second portion 111d may be equal to, for example, 0.3 to 0.8 segment widths. In some embodiments, the length of the second portion 111d may be equal to, for example, 0.3, 0.4, 0.5, 0.6, 0.7 or 0.8 segment widths.

As shown in FIG. 4a, when the end portions of the occlusion structure 111 at the first distal end 111b are gathered to abut against one another, the second and first portions 111d, 111c of the occlusion structure 111 and the traction structure 112 together provide balanced leverage so that the occlusion structure 111 achieves a self-stabilizing equilibrium and will not roll inwardly any more unless the traction structure 112 experiences a tension force that is sufficiently large or strength of the traction structure 112 is higher than that of the occlusion structure 111. In this configuration, the occlusion structure 111 will not further roll inwardly even when the traction structure 112 is tensioned to break. Therefore, the abutting of the end portions of the second portion 111d against one another can effectively block further retraction of the control shaft 220. In other words, the connection point of the traction structure 112 to the occlusion structure 111 may be located not just at the first distal end 111b of the occlusion structure 111 but a distance from the first distal end 111b, so that the end portions at the first distal end 111b can be gathered and abut against one another under the traction of the traction structure 112, thus providing resistance to further retraction. In this way, the occluding stent 110 can have mechanical self-limiting capabilities, which prevent entanglement of the LAA occluder 100 caused by over-retraction during its retrieval and allow an increased surgical success rate.

Alternatively, as shown in FIG. 4b, the gathered end portions of the occlusion structure 111 at the first distal end 111b may not abut against one another. Rather, since the end portions of the occlusion structure 111 at the first distal end 111b are mesh cells, the second portion 111d may cross over one another in such a manner that the projections in each pair of opposing projections in the second portion 111d insert into and are pushed against each other. This may also stop further retraction of the control shaft 220.

The advantages provided by preferred embodiments of the present invention will be described in detail below with additional reference to FIGS. 5a to 5c, which show an LAA occluder as a comparative example. For the sake of brevity, components are shown in a simplified and schematic manner in FIGS. 5a to 5c or omitted therefrom. However, those skilled in the art can know how they are implemented from the teachings of this application and available knowledge.

Figure 5A:
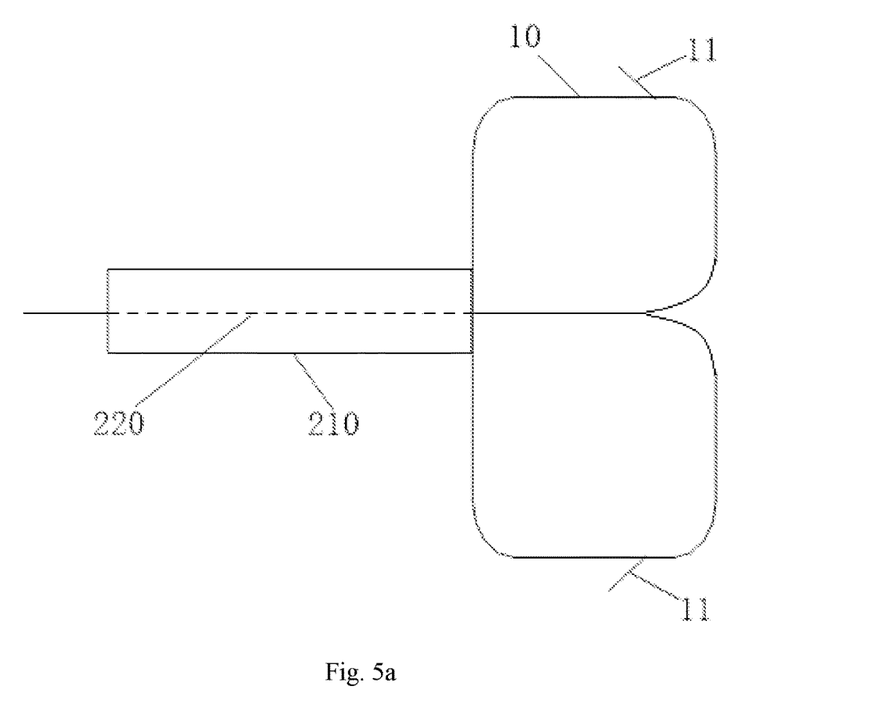
FIG. 5a is a simplified schematic diagram of an assembly of an LAA occluder as a comparative example and a delivery device coupled thereto, according to an embodiment of the present invention.
Figure 5B:
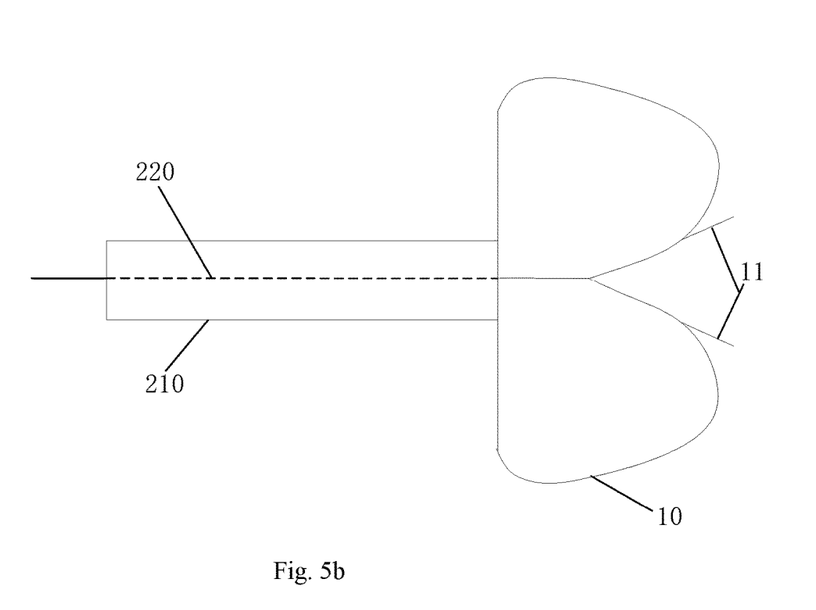
FIG. 5b is a schematic diagram of the LAA occluder of FIG. 5a, with a distal end portion thereof driven by the delivery device to assume a collapsed configuration where entanglement of the distal end portion of the LAA occluder has not taken place yet.
Figure 5C:
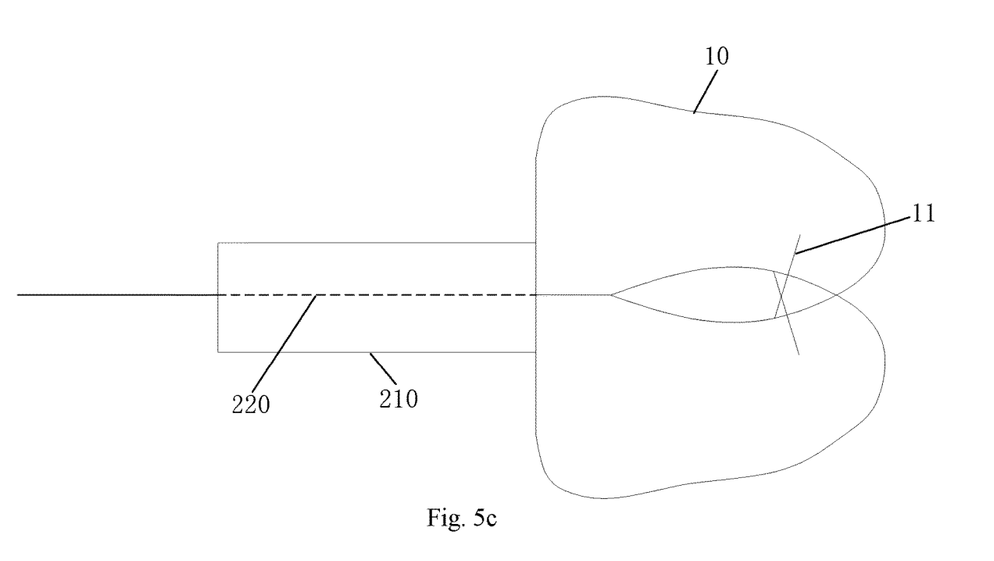
FIG. 5c is a schematic diagram of the LAA occluder of FIG. 5b, with a distal end portion thereof in which entanglement has taken place as a result of an additional driving action of the delivery device.

As shown in FIGS. 5a to 5c, the comparative example is assumed to not include the second portion 111d, with the connection point of the traction structure 112 to the occlusion structure 111 being located just at the first distal end 111b of the occlusion structure 111. In this example, the occluding stent 10 is also coupled detachably to the control shaft 220 at the distal end and to the hollow push tube 210 at the proximal end. Therefore, in practical use, distal end portions of the occluding stent 10 can also be gathered by retracting the control shaft 220. However, the inventors have found that this occluding stent 10 tends to encounter the problem of entanglement during its retrieval.

Figure 7:
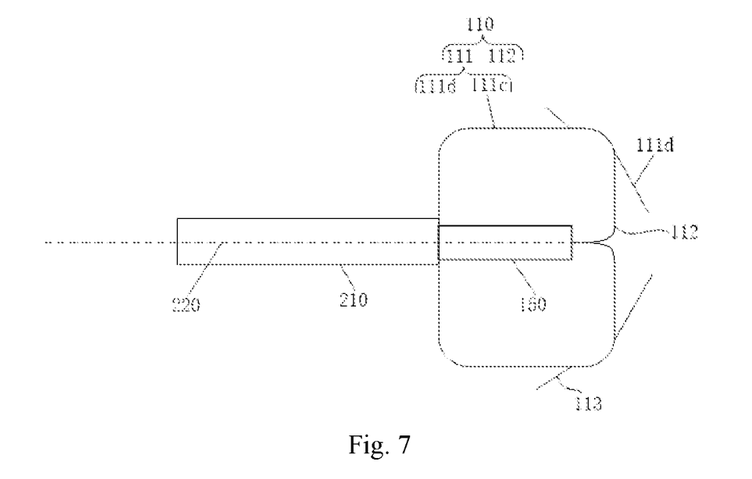
FIG. 7 is a simplified schematic diagram of an LAA occluder according to a preferred embodiment of the present invention, which is assembled with a delivery device.
Figure 8:
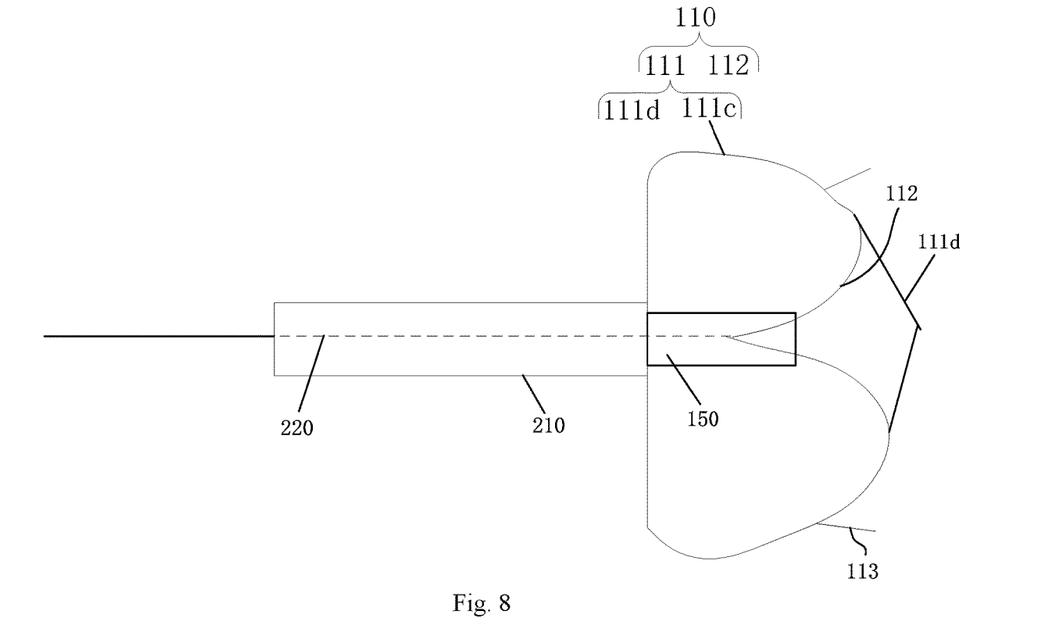
FIG. 8 is a simplified schematic diagram of an LAA occluder according to a preferred embodiment of the present invention, with distal end portions thereof abutting against one another as a result of a driving action of a delivery device.

Specifically, in the retrieval process, the control shaft 220 tends to be over-retracted a distance exceeding its maximum permissible stroke due to human error, thus possibly causing the problem of entanglement as a result of inward rolling of the occluding stent 10 itself and anchors 11 thereon. This is because the retrieval relies mainly on manual control of movement of the control shaft 220 (such movement is associated with a theoretical position limit, and the aforementioned problem tends to take place when the limit is exceeded). As a result, the retrieval control involves much subjectivity, is low in reliability, and cannot effectively ensure a sufficient surgical success rate. In order to overcome this, as shown in FIG. 7, according to preferred embodiments of the present invention, a trialing section (i.e., the second portion 111d) is added to the distal end of the occluding stent 10 to impart mechanical limiting capabilities to the occlusion structure 111, which allow the end portions of the occlusion structure 111 at the first distal end 111b to be gathered and preferably abut against one another (as shown FIG. 8) when the control shaft 220 is retracted to an appropriate position, thus making the control shaft 220 impossible to be retracted any more. This limiting mechanism is highly reliable and can effectively avoid the problem of entanglement of the occlusion structure and result in an increased surgical success rate. FIG. 7 is a schematic illustration of the LAA occluder 100 assembled with the delivery device 200 according to preferred embodiments of the present invention, and FIG. 8 shows the assembled LAA occluder 100 and the delivery device 200 according to preferred embodiments of the present invention, with the distal end portions of the LAA occluder 100 being abutting against one another under a driving action of the delivery device 200. Similarly, components are shown in a simplified form in these two figures or omitted therefrom, but those skilled in the art can know, from the teachings of this application and available knowledge, how they are implemented and what their advantages are.

In particular, before the LAA occluder 100 of the present invention is completely released in the body of a patient, if the operator finds that the release would result in undesired implantation of the occluder, for example, to a too shallow or deep depth or with an inclined orientation, the LAA occluder 100 can be retrieved and repositioned at least by means of the delivery device 200. According to embodiments of the present invention, the retrieval and repositioning of the LAA occluder 100 can be accomplished in the following two ways:

1) Direct Adjustment of the Occluding Stent's Position

At first, with the proximal securing member 120 being kept stationary, the control shaft 220 is manipulated to drive the distal securing member 130 to move toward the proximal securing member 120 so that the occluding stent 110 is further contracted (if possible, this may release the coupling of the occluding stent 110 to the inner wall of the LAA, such as attachment or anchoring). The hollow push tube 210 is then pushed to make an adjustment in the position of the occluding stent 110 in the LAA. Once the occluding stent 110 has been tuned to a desired position, the control shaft 220 is withdrawn, and the distal securing member 130 will move backwards under the action of the elasticity of the occluding stent 110 and then stop somewhere. At this point, the retrieval and repositioning of the occluder are achieved. It is to be noted that the backward movement may re-establish the coupling of the occluding stent 110 to the inner wall of the LAA, resulting in securing of the occluding stent 110. For example, as a result of gradual spring-back of the distal end portions of the occluding stent 110, the anchors on the occluding stent 110 will come into contact with and pierce into the tissue of the inner wall of the LAA. On the contrary, contraction of the occluding stent 110 will pull the anchors out of the tissue of the inner wall of the LAA.

2) Indirect Adjustment of the Delivery Sheath's Position

First of all, with the proximal securing member 120 being kept stationary, the control shaft 220 is manipulated to drive the distal securing member 130 to move toward the proximal securing member 120 so that the occluding stent 110 is further contracted. Upon the occluding stent 110 shrinking to a proper size, the occluding stent 110 is partially or entirely retrieved into the delivery sheath with the aid of the hollow push tube 210. Afterward, when the delivery sheath is tuned to a desired position, the occluding stent 110 is again pushed by the hollow push tube 210 out of, and thus released from, the delivery sheath at the distal end thereof, so that it is positioned and anchored in the left atrial appendage (LAA) S, as shown in FIG. 6, in order to close the LAA and prevent blood clots from passing through the LAA orifice.

Figure 6:
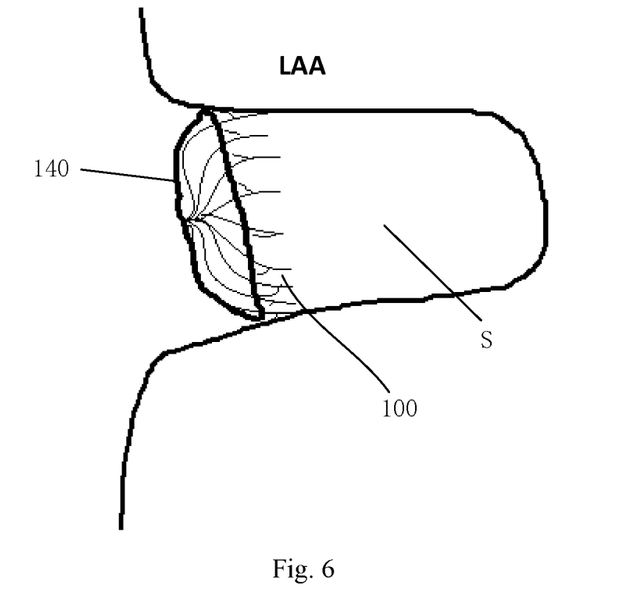
FIG. 6 is a schematic illustration of an LAA occluder according to an embodiment of the present invention, which is anchored in an LAA.

As shown in FIG. 6, in order for more effective closure of the LAA and more effective prevention of the passage of blood clots through the LAA orifice to be achieved, the LAA occluder 100 may further include an occluding membrane 140 configured to cover an internal or external surface of the occluding stent 110 or part thereof. The occluding membrane 140 may be made of a polymer material, and the occluding stent 110 may be a self-expanding stent made, preferably, of an elastic or super-elastic material and, more preferably, of a shape memory elastic material such as Nitinol. Further, the proximal and distal securing members 120, 130 are preferably made of a biocompatible material such as, for example, stainless steel, Nitinol, a titanium alloy or the like.

In addition, the occlusion structure 111 may include a plurality of mesh cells with many corner nodes. Preferably, the traction structure 112 is attached to the occlusion structure 111 at some of the corner nodes, and the number of the traction elements 1121 is smaller than or equal to that of corner nodes distributed on the same circumference of the occlusion structure 111. That is, not all the corner nodes on the same circumference may be connected to the traction structure 112. The number of the traction elements 1121 may be at least three such as, for example, without limitation, eight, as shown. Moreover, in order to provide strengthened structural support, the traction elements 1121 are preferably wires or struts that can be axially stressed. More preferably, the traction elements 1121 may be formed of a material selected from shape memory materials such as polymers or metal alloys.

Further, the distal securing member 130 may be detachably coupled to a fourth distal end 221 of the control shaft 220, for example, by threading, latching, snapping or the like, which provides the advantages of structural simplicity and facilitated retrieval. Controlling the contraction and deformation of the LAA occluder by means of the control shaft 220 that is independent of the hollow push tube 210 can simplify and facilitate the retrieval operation. Likewise, the hollow push tube 210 may be detachably coupled, at the third distal end 211, to the proximal securing member 120 by threading, latching, snapping or the like.

As shown in FIGS. 1 to 4, preferably, the LAA occluder 100 may further include a hollow guide member 150 configured to adjust the shape and orientation of the during retrieval. The hollow guide member 150 may have a second proximal end and a second distal end opposing the second proximal end. The second proximal end of the hollow guide member 150 may be coupled to the first proximal end 111a of the occlusion structure 111. Specifically, the hollow guide member 150 may be connected to the first portion 111c in such a manner that, prior to the gathering of the end portions (i.e., in an expanded configuration), the hollow guide member 150 is located between the proximal securing member 120 and the distal securing member 130 and is arranged coaxially with the proximal securing member 120 in order to allow insertion of the distal securing member 130 and at least part of the traction structure 112 into the hollow guide member 150 from the second distal end. In this way, the shape and direction of deformation of the occluding stent 110 can be controlled to facilitate retrieval. Further, the control shaft 220 inserted in the proximal securing member 120 may be further inserted through the hollow guide member 150 and then coupled to the distal securing member 130. As a result, when the control shaft 220 is retracted, the distal securing member 130 and part of the traction structure 112 may be pulled into the hollow guide member 150, thus limiting axial movement of the distal securing member 130 within the hollow guide member 150. This can ensure a desirable shape and orientation of the occluding stent 110 at the first distal end and hence successful retrieval. Therefore, it is necessary for the sizes of the distal securing member 130 and the traction structure 112 to be so designed to allow their passage through the lumen of the hollow guide member 150.

Figure 9:
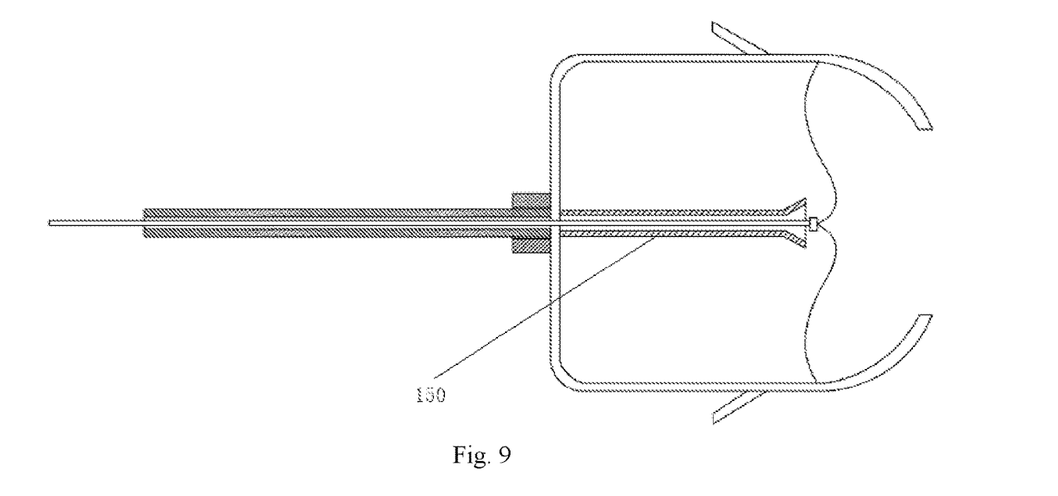
FIG. 9 is a schematic diagram of an LAA occluder and a delivery device coupled thereto according to an embodiment of the present invention, in which the second distal end of the hollow guide member has a flared opening.

The hollow guide member 150 may be made of a polymer or metal. In one preferred embodiment, as shown in FIG. 9, the hollow guide member 150 defines a flared opening at the second distal end, which is configured to facilitate smooth pull-in of the traction structure 112 to the hollow guide member 150. According to one preferred embodiment of the present invention, the length of the second portion 111d is preferably greater than an inner diameter of the hollow guide member 150. As such, when retracted by the traction structure 112, the second portion 111d will roll inwardly until it directly abuts against the distal end of the hollow guide member 150, thus blocking further entry of the second portion 111d into the hollow guide member 150. This can also provide the advantage of stopping further retraction of the control shaft 220.

Further, in order to more firmly secure the LAA occluder, either or both of the occlusion structure 111 and the traction structure 112 may be provided thereon with one or more anchors 113 configured to firmly secure the occluding stent 110 in the LAA with any displacement being effectively prevented and with ensured firmness by piercing into the tissue of the inner wall of the LAA. The anchors 113 may be barbs arranged at respective corner nodes of the mesh cells. However, the present invention is not limited to the case that only one anchor 113 is arranged at a single corner node. In one embodiment, along the axial direction, one or more rows of anchors 113 are arranged on the occluding stent 110. The anchors 113 can detach from the wall of the LAA upon retrieval of the occluding stent and can again fierce into the tissue of the inner wall of the LAA during spring-back of the occluding stent in the course of its re-release.

Obviously, in the expanded configuration of the occluding stent 110 according to embodiments of the present invention, in the axial direction thereof, the connection point of the traction structure 112 to the occlusion structure 111 is located farther away from the proximal securing member 120 than from the distal securing member 130. For example, the traction structure 112 may assume an umbrella-like shape having an opening facing the first distal end 111b. In other embodiments, it may also be configured that, in the expanded configuration, in the axial direction of the occluding stent, the connection point of the traction structure 112 to the occlusion structure 111 is located closer to the proximal securing member 120 than to the distal securing member 130. In this case, for example, the traction structure 112 may assume an umbrella-like shape having an opening facing the first proximal end 111a.

In addition, in the case with the opening of the traction structure 112 facing the first proximal end 111a, the second proximal end of the traction structure 112 (i.e., the end where the distal securing member 130 is arranged) may be located out of the occluding stent 110. However, for safety considerations, it is preferred that the second proximal end of the traction structure 112 does not extend beyond the first distal end 111b of the occlusion structure 111, in order to prevent bringing damage to the tissue due to an excessive length. Further, before the partial gathering of the occluding stent 110 at the first distal end 111b, the connection point of the traction structure 112 to the occlusion structure 111 may be aligned with the distal securing member 130 in the axial direction of the occluding stent.

It is to be noted that, in the case with the opening of the traction structure 112 facing the first proximal end 111a, the second end of the traction structure 112 where it is attached to the occlusion structure 111 is considered as its proximal end, while the first end thereof where it is coupled to the distal securing member 130 is considered as its distal end. In this case, the traction structure 112 is coupled at the distal end to the distal securing member 130. On the contrary, in the case with the opening of the traction structure 112 facing the first distal end 111b, the second end of the traction structure 112 where it is attached to the occlusion structure 111 is considered as its distal end, while the first end thereof where it is coupled to the distal securing member 130 is considered as its proximal end. In this case, the traction structure 112 coupled at the proximal end to the distal securing member 130.

In embodiments of the present invention, there is also provided a left atrial appendage (LAA) occlusion system including the LAA occluder 100 and the delivery device 200 as defined above. The delivery device 200 includes the hollow push tube 210 and the control shaft 220. The hollow push tube 210 is detachably coupled to the proximal securing member 120 in order to allow delivery and release of the LAA occluder 100. The control shaft 220 is inserted through the hollow push tube 210 and the proximal securing member 120 and is detachably coupled to the distal securing member 130 in order to allow retrieval and release of the LAA occluder 100.

While different variants of the occluding stent have been described in detail with reference to the foregoing embodiments, it is a matter of course that the present invention includes, but is not limited to, the above variants discussed hereinabove, and any change made thereto is intended to also fall within the scope of the present invention. Other embodiments are possible for those skilled in the art in light of the above embodiments.

In summary, in the occluding stent according to embodiments of the present invention, each of the occlusion and traction structures is coupled to a respective one of the securing members. The distal securing member coupled to the traction structure can move relative to the proximal securing member coupled to the occlusion structure to result in a reduction in the axial length of the occluding stent. As a result, the length of the delivery device can be shortened with lower cost, reduced surgical difficulty and shorter surgical time.

Moreover, according to the present invention, in addition to a reduction in the axial length of the occluding stent, the movement of the distal securing member toward the proximal securing member can also result in a reduced outer diameter of the occluding stent, which can facilitate retrieval of at least part of the occluding stent into the delivery sheath during release and subsequent re-positioning and re-release thereof. Additionally, this can keep the anchors on the occluding stent away from the inner wall of the LAA under the action of the distal securing member, avoiding bringing damage to the tissue or muscle during repeated re-positioning and retrieval and assuring safety and reliability of the retrieval operation.

Notably, according to the present invention, when the end portions of the occlusion structure are gathered at the first distal end as a result of the movement of the distal securing member toward the proximal securing member, further movement of the distal securing member (i.e., further retraction of the control shaft) will be blocked. This can avoid the problem of entanglement resulting from inward rolling of the occluding stent in the event of human error, resulting in an additional increase in surgical success rate.

The description presented above is merely that of a few preferred embodiments of the present invention and does not limit the scope thereof in any sense. Any and all changes and modifications made by those of ordinary skill in the art based on the above teachings fall within the scope as defined in the appended claims.

What is claimed is:

1. A left atrial appendage occluder, comprising an occluding stent,
   a proximal securing member and a distal securing member,
      the occluding stent comprising an occlusion structure and a traction structure, the occlusion structure having a first proximal end and a first distal end opposing the first proximal end, the proximal securing member disposed at the first proximal end and configured to form a closed configuration at the first proximal end, the first distal end configured in an open configuration, the traction structure attached to the occlusion structure and at least partially overlapped with the occlusion structure along an axial direction, the traction structure comprising a plurality of traction elements each having a first end connected to the distal securing member and a second end connected to the occlusion structure, wherein movement of the distal securing member toward the proximal securing member is able to cause the occluding stent to transition from an expanded configuration to a collapsed configuration,
      wherein the occlusion structure is divided into a first portion and a second portion with a connection point of the traction structure to the occlusion structure serving as a boundary, the first portion is located on one side of the boundary, and the second portion is located on the other side of the boundary, the connection point is disposed between the first portion and the second portion along the axial direction,
      wherein the occlusion structure comprises a plurality of mesh cells, at least one of the plurality of mesh cells distal to the connection point,
      wherein a length of the second portion is equal to 3% to 30% of a total length of the occlusion structure.

2. The left atrial appendage occluder according to claim 1, wherein the second portion is joined to the first portion along the axial direction, the first portion providing the first proximal end, the second portion providing the first distal end.

3. The left atrial appendage occluder according to claim 1, wherein the length of the second portion is equal to 3% to 30% of an outer diameter of the occlusion structure.

4. The left atrial appendage occluder according to claim 1, wherein a length of the second portion corresponds to 0.1 to 1.0 axial length of each mesh cell of the occlusion structure.

5. The left atrial appendage occluder according to claim 1, wherein the second portion is one or a combination of a tapered structure, a straight structure and a flared structure.

6. The left atrial appendage occluder according to claim 5, wherein a distalmost end of the second portion is a tapered structure.

7. The left atrial appendage occluder according to claim 1, further comprising a hollow guide member coupled to the occlusion structure, the hollow guide member arranged coaxially with the proximal securing member so as to allow passage of the distal securing member and at least part of the traction structure therethrough.

8. The left atrial appendage occluder according to claim 7, wherein the hollow guide member has a second proximal end and a second distal end opposing the second proximal end, the second proximal end coupled to the first proximal end of the occlusion structure, and wherein the distal securing member and the at least part of the traction structure are able to be inserted into the hollow guide member from the second distal end, the second distal end having a flared opening.

9. The left atrial appendage occluder according to claim 7, wherein the hollow guide member has an inner diameter smaller than a length of the second portion.

10. The left atrial appendage occluder according to claim 1, wherein the traction structure is completely overlapped with the occlusion structure along the axial direction.

11. The left atrial appendage occluder according to claim 1, wherein the occlusion structure further comprises a plurality of projections at the first distal end, the plurality of projections abutting against one another, to limit the movement of the distal securing member toward the proximal securing member under traction of the traction structure.

12. The left atrial appendage occluder according to claim 1, wherein the connection point of the traction structure to the occlusion structure is aligned with the distal securing member along the axial direction.

13. The left atrial appendage occluder according to claim 1, wherein the plurality of mesh cells each having a plurality of corner nodes, and wherein a number of the traction elements is smaller than or equal to that of the plurality of corner nodes on a same circumference of the occlusion structure.

14. The left atrial appendage occluder according to claim 1, further comprising an occluding membrane, which covers at least part of an internal or external surface of the occluding stent, the occlusion structure and/or the traction structure provided thereon with an anchor for securing the left atrial appendage occluder to an inner wall of a left atrial appendage.

15. The left atrial appendage occluder according to claim 1, wherein the occlusion structure is molded integrally with, or separately from, the traction structure, and wherein the distal securing member is arranged coaxially with the proximal securing member.

16. The left atrial appendage occluder according to claim 1, wherein the boundary extends in a direction substantially perpendicular to the axial direction.

17. A left atrial appendage occlusion system, comprising the left atrial appendage occluder as defined in claim 1 and a delivery device, the delivery device comprising a hollow push tube and a control shaft, the hollow push tube detachably coupled to the proximal securing member in order to allow delivery and release of the left atrial appendage occluder, the control shaft inserted through the hollow push tube and the proximal securing member and detachably coupled to the distal securing member in order to allow retrieval and release of the left atrial appendage occluder.

18. The left atrial appendage occlusion system according to claim 17, wherein the hollow push tube has a third distal end configured for connection with the proximal securing member by threading, latching or snapping, and wherein the control shaft has a fourth distal end configured for connection with the distal securing member by threading, latching or snapping.

* * * * *